United States Patent [19]

Ganci

[11] 4,438,102

[45] Mar. 20, 1984

[54] METHOD OF PROMOTING TISSUE GROWTH

[75] Inventor: Salvatore Ganci, New York, N.Y.

[73] Assignee: Ciro's Touch, Ltd., New York, N.Y.

[21] Appl. No.: 406,869

[22] Filed: Aug. 10, 1982

[51] Int. Cl.$^3$ .................. A61K 31/19; A61K 33/40
[52] U.S. Cl. ........................... 424/130; 424/317; 424/DIG. 13
[58] Field of Search .............. 424/130, 317, DIG. 13

[56] References Cited

U.S. PATENT DOCUMENTS 3,954,974  5/1976  Herzog .......................... 424/130

4,195,095  3/1980  Sheffner ........................ 424/317

OTHER PUBLICATIONS

Merck Index, 9th Ed., 1976, p. 1205, (Para. 9070).

*Primary Examiner*—Leonard Schenkman
*Attorney, Agent, or Firm*—Wyatt, Gerber, Shoup, Scobey & Badie

[57] ABSTRACT

Compositions containing gelatin, hydrogen peroxide, ammonium hydroxide, thioglycolic acid, and a lower alkanol as the principal ingredients are useful to promote the growth of dermal and epidermal tissue.

14 Claims, No Drawings

METHOD OF PROMOTING TISSUE GROWTH

This invention relates to methods of treating mammals, including humans, to promote the growth of normal dermal and epidermal tissue with patients in need of such treatment.

Many diseases and afflictions of mammals including humans require rapid regeneration of normal healthy endothelium and epithelium. These include various physical trauma such as cuts, burns, dermatological dysfunction and abrasions; infection leading to eruptions such as ulcers or boils; acne; seborrhea; contact dermatitis; and infections such as herpes simplex infections and athletes foot. Generally speaking, the more rapidly the normal endothelium and epithelium can be regenerated, the more rapid the return to normal health and well being.

It has now been discovered that the growth of such normal healthy tissue can be promoted by topical application of certain compositions to the area of the mammalian body in need of such promotion. The compositions to be hereinafter described may be used to promote the healing of the skin following lacerations, including surgical lacerations; burns or other thermal damage, dermatological disorders such as contact dermatitis, rashes and skin lesions; and abrasions. They have been used to promote the growth of healthy gum tissue following periodontal surgery.

The compositions used in the practice of this invention contain thioglycolic acid, ammonium hydroxide, glycerine, citric acid, hydrogen peroxide, a lower alkanol, a solvent and gelatin. The compositions may also contain various other inert additives such as a perfume or coloring agent.

The presently preferred procedure for preparing the compositions of this invention is to prepare a first mixture containing thioglycolic acid and ammonium hydroxide, and a second mixture containing the other ingredients. The two mixtures are then blended into a mixture to which additional gelatin may be added, and the concentration of the various ingredients in the resulting blend adjusted by the addition of water.

The first mixture may be prepared by the addition of sufficient aqueous ammonium hydroxide to thioglycolic acid to produce a product with a pH of from about 8.7 to 11, preferably 9.6 to 9.8. Normally dilute aqueous ammonium hydroxide, e.g. about 2% to 8% is employed. The resulting composition will contain from about 65% to 85% dilute ammonium hydroxide, preferably 78% to 82% dilute ammonium hydroxide.

The second mixture is prepared by mixing the listed ingredients with water.

The gelatin employed in readily available in the market place. It is a hydrolysis product obtained by partial acid or basic hydrolysis of the collagen of skin, white connective tissue, bones and hooves of animals. Various grades of gelatin are available. The presently preferred is Grade A edible gelatin, although other grades can be employed. All of the gelatin may be taken up in the second mixture. Alternatively a portion of it may be included in the first mixture.

The final compositions employed in this invention will contain from 25% to 40% by weight of the first mixture containing the ammonium hydroxide and thioglycolic acid together with the following ingredients in percent by weight based on the total weight of the final compositions.

Glycerine: 0.15 to 0.25%
Citric Acid: 0.095 to 0.29%
Hydrogen peroxide: 0.0097 to 0.014%
Solvent: 0.39 to 0.78%
Lower Alkanol: 0.78 to 1.95%
Gelatin: 1.17 to 2.73%

The hydrogen peroxide may or may not be stabilized. Normally, for the preparation of the compositions of the invention it will be in the form of a dilute solution when added to the second mixture. Typically, the concentration in the dilute solution will be from 2 to 5%, and sufficient solution will be employed to provide the above described proportion of hydrogen peroxide.

The preferred solvents are polar organic solvents such as ketones, ethers and amines. Acetone is preferred, but ethers such as diethyl ether or dipropyl ether can also be employed. Amines such as trimethyl or triethyl amine are useful.

The term "lower alkanol" as employed in this description and claims refer to alcohols containing only carbon, hydrogen and oxygen up to a total of about four carbon atoms. The preferred alkanols are water soluble alkanols such as methyl or ethyl alcohol.

The following non-limiting examples are given by way of illustration only.

EXAMPLE 1

FIRST MIXTURE

To 32 ounces of thioglycolic acid was added a sufficient amount of 3% ammonium hydroxide to produce an aqueous composition with a pH of about 9.6

SECOND MIXTURE

A mixture was prepared containing 0.75 ounces glycerine, 0.25 ounces citric acid, 1.5 ounces of 3% hydrogen peroxide, 1.0 ounce of acetone and 3 ounces of ethanol. The mixture in a glass container is stirred with a glass rod while adding 3.0 ounces of Grade A unscented edible gelatin. To this mixture 32 ounces of very hot water is added to dissolve the gelatin. One ounce of orange French Guinea Oil is added, and the mixture is made up to one gallon by the addition of water.

FINAL PRODUCT

The final composition was prepared by blending 20 ounces of the first mixture with 66 ounces of the second mixture and adding 1.5 ounces of gelatin together with a perfume and colorant.

EXAMPLE 2

H. a young girl cut the webbing between her thumb and index finger. The cut was deep and bleeding profusely. The cut was washed extensively with water, then with a gauze soaked with a composition of this invention. The cut required eight stitches. Four days later she was seen by a physician, and the wound was sufficiently healed to permit removal of the stitches. This was three days earlier than usual. The wound was closed and a small scar was formed. The area adjacent to the original cut was still somewhat red and swollen, but clearly healing.

EXAMPLE 3

J. T., a female plagued with seborrhea for over 30 years followed a course of treatment in which the affected area was rinsed every night for a week with a composition of the invention which was allowed to dry on the treated surface. At the end of the week there was no itch, no flushing and no exacerbate.

EXAMPLE 4

K. H., a 33 year old female was bothered with a recurring rash of undiagnosed origin on her arms. It was itchy and characterized by white dots on an inflamed background. She was treated for eight days with gauze patches, soaked with a composition of this invention on each arm. At the end of this period the rash had disappeared. She stated that nothing else that she had tried was effective.

EXAMPLE 5

D. S., an adult female had undergone periodontal surgery two years prior to treatment. New tissue was very slow in regenerating. There was a visible and annoying cleft between the top middle teeth. There was some pain. Treatment was effected by swishing a small amount of a composition of this invention over the gums twice daily. At the end of the second day the pain had disappeared. After two weeks treatment the cleft had almost completely disappeared. Other gaps in the gum structure were also alleviated.

EXAMPLE 6

A 31 year old male construction worker burned his forearm with a torch. He was treated by washing daily with a composition of the invention. The dressings were changed daily. The burn had almost disappeared in three days, and totally disappeared in ten days.

EXAMPLE 7

A four and one half year old girl cut and scraped her knee while playing. The cut was 2.5 inches long, bleeding freely and could be separated one quarter to one half inch. She was treated with gauze soaked in a composition of this invention and bandaged. In only four days the abrasion was neither red or inflamed. The cut was closed, but not healed. The cut had healed to the point where it was barely visible after seven days.

EXAMPLE 8

A 26 year old male was aflicted with recurring Herpes simplex I cold sores. One such sore in the lower right corner of his mouth was red, weeping and caused sever itching. Treatment was effected topically with a composition of the invention four times a day. At the end of two days the lesion was definitely healing. There was no itch and no weeping. At the end of five days the lesion was barely visible. This was a result which the patient had observed only after treatment for as long as two weeks with previous sores.

What is claimed is:

1. A method of promoting the growth of normal dermal and epidermal tissue in mammals which comprises topical treatment of a mammal in need of such promotion with a composition comprising from 25 to 40% by weight of a mixture containing thioglycolic acid and 65% to 85% dilute ammonium hydroxide at a pH of from 8.5 to 11 together with:
    Glycerine: 0.15 to 0.25%
    Citric Acid: 0.095 to 0.29%
    Hydrogen Peroxide: 0.0097 to 0.014%
    Solvent: 0.39 to 0.78%
    Lower Alkanol: 0.78 to 1.95%
    Gelatin: 1.17 to 2.73%
and water, all percentages pased on the total weight of the composition.

2. A method as in claim 1 wherein the mammal is human.

3. A method as in claim 1 wherein the need for promoting the growth of tissue arises from a determatological disorder.

4. A method as in claim 3 wherein the dermatological disorder is contact dermatitis.

5. A method as in claim 3 wherein the dermatological disorder is a rash.

6. A method as in claim 1 wherein the need for promoting the growth of tissue arises from seborrhea.

7. A method as in claim 1 wherein the need for promoting the growth of tissue arises from a laceration.

8. A method as in claim 7 wherein the laceration is a surgical laceration.

9. A method as in claim 1 wherein the need for promoting the growth of tissue arises from an abrasion.

10. A method as in claim 1 wherein the need for promoting the growth of tissue arises from thermal damage to the tissue.

11. A method as in claim 1 wherein the peroxide is stabilized hydrogen peroxide.

12. A method as in claim 1 wherein the lower alkanol is ethanol.

13. A method as in claim 1 wherein the solvent is acetone.

14. A method as in claim 1 wherein the alkanol is ethanol and the solvent is acetone.

* * * * *